(12) United States Patent
Oren et al.

(10) Patent No.: US 9,155,534 B2
(45) Date of Patent: Oct. 13, 2015

(54) SIDE-LOADED MEDICAL IMPLEMENT PARTICULARLY USEFUL IN ARTHROSCOPIC SURGERY

(75) Inventors: Ran Oren, Doar-Na Oshrat (IL); Eran Zakai, Doar-Na Misgav (IL); Yaron Fuerst, Kfar-Vradim (IL); Aryeh Mirochinik, Akko (IL); Ian Crookenden, Franklin, MA (US); Kevin McKenney, Needham, MA (US); Meghan Scanlon, Duxbury, MA (US); Makoto Ohira, Westborough, MA (US)

(73) Assignee: DePuy Mitek Inc., Raynham, MA (US)

( * ) Notice: Subject to any disclaimer, the term of this patent is extended or adjusted under 35 U.S.C. 154(b) by 0 days.

(21) Appl. No.: 13/201,864

(22) PCT Filed: Feb. 17, 2010

(86) PCT No.: PCT/IL2010/000141

§ 371 (c)(1),
(2), (4) Date: Aug. 17, 2011

(87) PCT Pub. No.: WO2010/095132

PCT Pub. Date: Aug. 26, 2010

(65) Prior Publication Data

US 2011/0301621 A1  Dec. 8, 2011

Related U.S. Application Data

(60) Provisional application No. 61/152,982, filed on Feb. 17, 2009.

(51) Int. Cl.
*A61B 17/04* (2006.01)
*A61B 19/00* (2006.01)
*A61B 17/06* (2006.01)

(52) U.S. Cl.
CPC ............ *A61B 17/0483* (2013.01); *A61B 19/42* (2013.01); *A61B 17/0485* (2013.01); *A61B 17/06109* (2013.01)

(58) Field of Classification Search
CPC ........... A61B 17/0483; A61B 17/0485; A61B 17/0469; A61B 17/0482; A61B 1/00066
USPC .................................................. 606/144–148
See application file for complete search history.

(56) References Cited

U.S. PATENT DOCUMENTS 3,840,017 A    10/1974  Violante
5,562,683 A *  10/1996  Chan ............................. 606/139
(Continued)

FOREIGN PATENT DOCUMENTS

DE    102005015687    10/2006
DE    202008011769    11/2008
(Continued)

OTHER PUBLICATIONS

International Preliminary Report on Patentability Dated Sep. 1, 2011 From the International Bureau of WIPO Re. Application No. PCT/IL2010/000140.

(Continued)

*Primary Examiner* — Alexander Orkin

(57) ABSTRACT

A medical implement particularly useful in arthroscopic surgery, includes: a handle having a proximal end configured for manual gripping by a user, a distal end for manipulation during the surgery, an internal passageway extending through the handle from the proximal end to the distal end thereof, and a longitudinally-extending slot extending longitudinally through the handle from its outer surface to the passageway for side-loading the handle with a manipulatable member to be manipulated during surgery. A shield is located within the passageway in the handle. The shield is secured along one edge to the inner surface of handle defining the passageway, and includes an elastic section normally covering the longitudinally-extending slot. The elastic section of the shield is yieldable to permit side-loading of the manipulatable member into the passageway, but to prevent a side-loaded manipulatable member from passing outwardly from the passageway.

14 Claims, 4 Drawing Sheets

(56) References Cited

U.S. PATENT DOCUMENTS

| | | | |
|---|---|---|---|
| 5,643,292 A * | 7/1997 | Hart | 606/144 |
| 5,681,331 A * | 10/1997 | de la Torre et al. | 606/148 |
| 5,755,728 A * | 5/1998 | Maki | 606/145 |
| 6,213,375 B1 | 4/2001 | Rybicki | |
| 6,511,488 B1 * | 1/2003 | Marshall et al. | 606/148 |
| 7,329,264 B2 | 2/2008 | Merves | |
| 7,704,262 B2 | 4/2010 | Bellafiore et al. | |
| 2004/0106935 A1 * | 6/2004 | Merves | 606/139 |
| 2005/0165416 A1 * | 7/2005 | Bojarski et al. | 606/144 |
| 2005/0283171 A1 | 12/2005 | Bellafiore et al. | |
| 2006/0069399 A1 | 3/2006 | Weisel et al. | |
| 2006/0178682 A1 * | 8/2006 | Boehlke | 606/148 |
| 2006/0229642 A1 * | 10/2006 | Oberlaender et al. | 606/148 |
| 2008/0221619 A1 * | 9/2008 | Spivey et al. | 606/232 |
| 2008/0275477 A1 * | 11/2008 | Sterrett et al. | 606/148 |
| 2010/0057111 A1 | 3/2010 | Berberich et al. | |
| 2011/0301622 A1 | 12/2011 | Oren et al. | |

FOREIGN PATENT DOCUMENTS

| | | |
|---|---|---|
| EP | 1709909 | 10/2006 |
| WO | WO 96/21394 | 7/1996 |
| WO | WO 2007/097994 | 8/2007 |
| WO | WO 2008/109625 | 9/2008 |
| WO | WO 2010/095131 | 8/2010 |
| WO | WO 2010/095132 | 8/2010 |

OTHER PUBLICATIONS

International Preliminary Report on Patentability Dated Sep. 1, 2011 From the International Bureau of WIPO Re. Application No. PCT/IL2010/000141.

International Search Report and the Written Opinion Dated Jul. 7, 2010 From the International Searching Authority Re.: Application No. PCT/IL2010/000141.

International Search Report and the Written Opinion Dated May 12, 2010 From the International Searching Authority Re.: Application No. PCT/IL2010/000140.

Office Action and Search Report Dated Mar. 22, 2013 From the State Intellectual Property Office of the People's Republic of China Re. Application No. 201080007977.6.

Translation of Notification of Office Action Dated Mar. 22, 2013 From the State Intellectual Property Office of the People's Republic of China Re. Application No. 201080007977.6.

Translation of Search Report Dated Mar. 22, 2013 From the State Intellectual Property Office of the People's Republic of China Re. Application No. 201080007977.6.

Office Action Dated May 2, 2013 From the Israel Patent Office Re. Application No. 214584 and Its Translation Into English.

Translation of Notification of Office Action Dated May 23, 2013 From the State Intellectual Property Office of the People's Republic of China Re. Application No. 201080007976.1.

Translation of Search Report Dated May 23, 2013 From the State Intellectual Property Office of the People's Republic of China Re. Application No. 201080007976.1.

Notice of Reasons for Rejection Dated Nov. 12, 2013 From the Japanese Patent Office Re. Application No. 2011-549733 and Its Translation Into English.

Notice of Reasons for Rejection Dated Jan. 7, 2014 From the Japanese Patent Office Re. Application No. P2011-549732 and Its Translation Into English.

Notification of Office Action Dated Jan. 20, 2014 From the State Intellectual Property Office of the People's Republic of China Re. Application No. 201080007976.1 and Its Translation Into English.

Office Action Dated Dec. 15, 2014 From the Israel Patent Office Re. Application No. 214233.

Official Action Dated Jan. 27, 2015 From the US Patent and Trademark Office Re. U.S. Appl. No. 13/201,867.

Requisition by the Examiner and the Examination Search Report Dated Feb. 17, 2015 From the Canadian Intellectual Property Office Re. Application No. 2,751,735.

Translation Dated Jan. 15, 2015 of Office Action Dated Dec. 15, 2014 From the Israel Patent Office Re. Application No. 214233.

Patent Examination Report Dated Jun. 18, 2014 From the Australian Government, IP Australia Re. Application No. 2010215109.

Official Action Dated Sep. 23, 2014 From the US Patent and Trademark Office Re. U.S. Appl. No. 13/201,867.

Notice of Reasons for Rejection Dated Sep. 30, 2014 From the Japanese Patent Office Re. Application No. P2011-549732 and Its Translation Into English.

Official Action Dated Jun. 17, 2014 From the US Patent and Trademark Office Re. U.S. Appl. No. 13/201,867.

Office Action Dated Oct. 10, 2013 From the -Israel Patent Office Re. Application No. 214584 and Its Translation Into English.

* cited by examiner

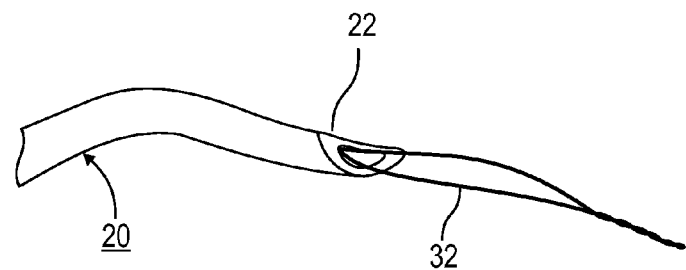
FIG. 5
   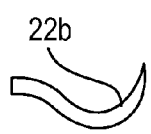   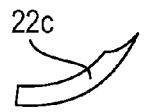   
FIG. 6A   FIG. 6B   FIG. 6C   FIG. 6D
      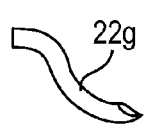
FIG. 6E   FIG. 6F   FIG. 6G

… (1)

SIDE-LOADED MEDICAL IMPLEMENT PARTICULARLY USEFUL IN ARTHROSCOPIC SURGERY

RELATED APPLICATIONS

This application is a National Phase of PCT Patent Application No. PCT/IL2010/000141 having International filing date of Feb. 17, 2010, which claims the benefit of priority of U.S. Provisional Patent Application No. 61/152,982 filed on Feb. 17, 2009. The contents of the above applications are all incorporated herein by reference.

FIELD AND BACKGROUND OF THE INVENTION

The present invention relates to side-loaded medical implements particularly useful in arthroscopic surgery. The invention is especially useful with respect to medical implements for manipulating sutures as described in a concurrently filed PCT Application. The invention is therefore described below especially with respect to such an embodiment.

In minimally invasive surgery, such as arthroscopic surgery, all operations must be performed through a narrow opening, the size of which limits the size of the instruments used and the free space available to manipulate them. Small-size cutting, grasping, debriding and stitching instruments, capable of operating through small portals, have been developed for this purpose.

Internal suturing is necessary in many arthroscopic procedures, in order to close wounds, repair tissue tears, or to reattach tissue which becomes detached from its normal position. A strand of suture must be applied to the location to be sutured, and the suture must then be passed through a layer of tissue and retrieved from the exit side. In other cases sutures attached to an anchoring element must be captured and passed through tissue.

Many suture passing and stitching devices are available to the arthroscopist. For example, U.S. Pat. No. 5,499,991, U.S. Pat. No. 5,222,977, as well as catalogs of Linvatec-Concept Inc., Arthrex Inc., DePuy Mitek Inc. and others describe and advertise such devices. All these devices are limited either to a part of the functions necessary, or in directions of approach, or in maneuverability in limited space.

OBJECTS AND BRIEF SUMMARY OF THE INVENTION

An object of the present invention is to provide a side-loaded medical implement having a number of advantages which make it particularly useful in arthroscopic surgery, especially with respect to the medical implement described in the above-identified, commonly-owned and concurrently-filed patent application, but also useful in other applications, such as in other minimally-invasive surgical procedures.

According to a broad aspect of the present invention, there is provided a medical implement comprising a handle having a proximal end configured for manual gripping by a user, a distal end for manipulation during the surgery, an internal passageway extending through the handle from the proximal end to the distal end thereof, and a longitudinally-extending slot extending longitudinally through the handle from its outer surface to the internal passageway for side-loading the handle with a manipulatable member to be manipulated during surgery; and a shield located within the passageway in the handle; the shield being secured along one edge to the inner surface of handle defining the passageway, and including an elastic section normally covering the longitudinally-extending slot; the elastic section of the shield being yieldable to permit side-loading of the manipulatable member into the passageway, but preventing a side-loaded manipulatable member from passing outwardly from the passageway.

In the preferred embodiment of the invention described below, the handle includes a hook formation extending longitudinally in the internal surface of the handle and open at one side for receiving and securing the one edge of the shield within the handle.

As indicated above, the invention is especially useful in medical implements of the type described in the above-identified currently-filed patent application, and is therefore described below with respect to this embodiment. In this embodiment, the shuttle includes a long flexible wire having a proximal end extending outwardly of the proximal end of the handle, and a distal end formed with a loop defining the suture-receiving element and extending outwardly of the distal end of the shaft.

As will be described below, the shield is very effective to facilitate side-loading the handle.

BRIEF DESCRIPTION OF THE DRAWINGS

The invention is herein described, by way of example only, with reference to the accompanying drawings, wherein

FIG. 5 is an enlarged view of the distal end of the medical implement of FIG. 1, and particularly the wire loop projecting from the tip at the distal end;

FIGS. 6A, 6B, 6C, 6D, 6E, 6F and 6G are alternative configurations of the distal tip of the implement shown in FIG. 4;

Figure 1:
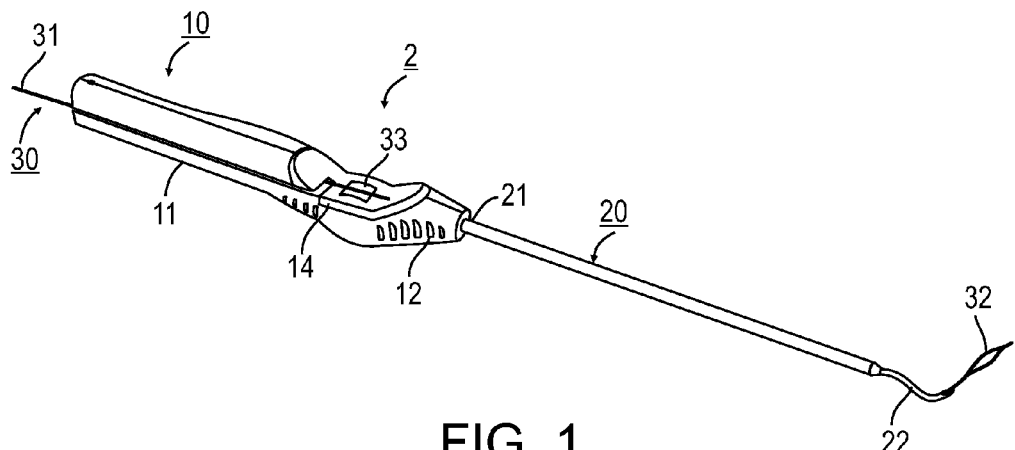
FIG. 1 is a perspective view of one preferred embodiment of a medical suture passing implement constructed according to the present invention for use in suturing within the shoulder.
Figure 2:
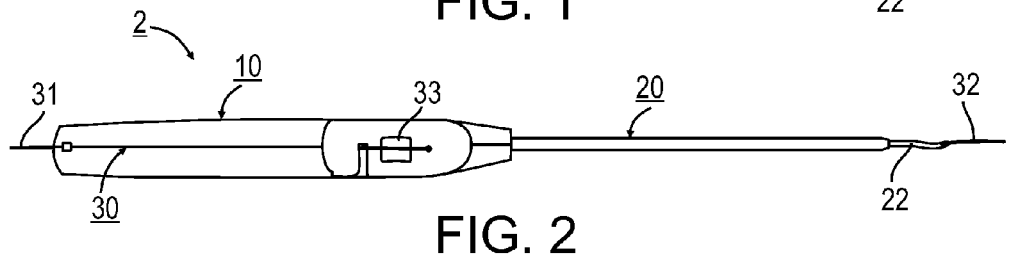
FIG. 2 is a top view of the implement of FIG. 1.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF A PREFERRED EMBODIMENT

Overall Construction

The medical implement illustrated in FIGS. 1-9 of the drawings, and therein generally designated 2, includes four main parts: a handle 10 having a proximal end 11 configured for manually grasping and a distal end 12; an elongated shaft 20 having a proximal end 21 joined to the distal end 12 of the handle, and a distal end formed with a pointed tip 22 for piercing tissue; a long flexible wire 30 receivable within, and manually moveable through, an interior passageway 13 (FIG. 4) of the handle at 10 and elongated shaft 20; and a shield member, generally designated 40 (illustrated particularly in FIGS. 7-9) to facilitate side-loading of the implement.

The long flexible wire 30 constitutes a shuttle for manipulating a suture, as will be disclosed more particularly below. It consists of two twisted strands having a proximal end 31 extending outwardly of the proximal end 11 of handle 10; a distal end twisted at its tip to form a loop 32 for receiving the suture to be passed through the tissue; and an intermediate portion 33 (FIG. 3) exposed for manual engagement by the thumb of user gripping the handle in order to extend or retract the distal loop 32.

Figure 3:
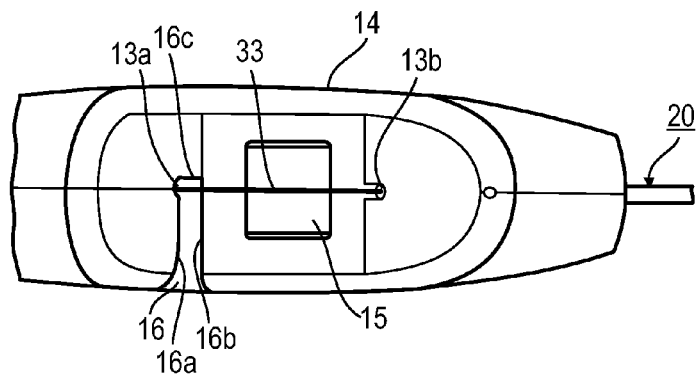
FIG. 3 is an enlarged fragmentary view of a portion of FIG. 2.
Figure 4:
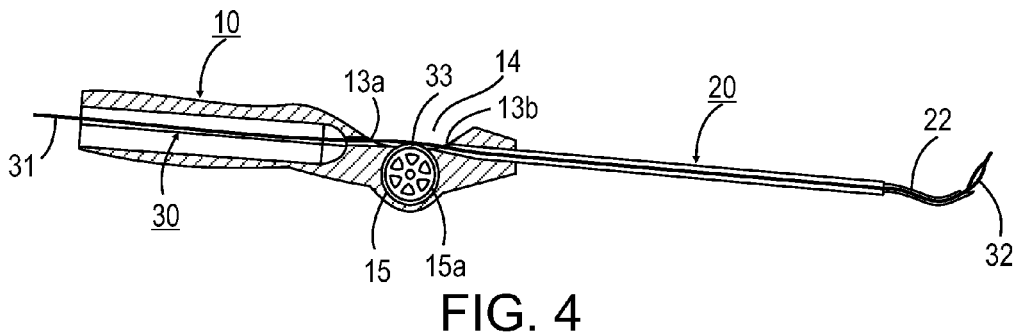
FIG. 4 is a sectional view along line V-V' in FIG. 2.

As shown particularly in FIGS. 3 and 4, handle 10 is formed, adjacent its distal end 12, with a recess 14 extending along the outer surface of the handle towards, but terminating short of, the distal end 12 of the handle. Recess 14 also extends inwardly from the outer surface to the passageway 13 through the handle receiving the long flexible wire 30 so as to expose the intermediate portion 33 of the wire to the thumb of the user grasping the handle.

In addition, the implement further includes a roller 15 rotatably mounted at 15a to the handle so as to underlie the exposed intermediate portion 33 of the long flexible wire 30 received within passageway 13 of the handle. Preferably, the outer surface of roller 15 is knurled or ribbed or is made of an elastomeric material, to enable the user, by pressing the exposed wire portion 33 against the roller, to rotate the roller in either direction in order to move the wire 30, particularly its distal loop 32, outwardly from the elongated shaft 20 to extend the distal loop, or inwardly into the elongated shaft to retract the distal loop.

As shown particularly in FIG. 3, handle 10 is further formed with a slot 16 having a longitudinally-extending section 16a extending along one side of the handle and terminating in a transversely-extending section 16b adjacent to recess 14 in the handle and spaced therefrom in the proximal direction. The longitudinally-extending section 16a of slot 16 extends from the proximal end 11 of handle 10 to the transversely-extending section 16b at the proximal side of recess 14. Slot 16 communicates with the interior passageway 13 of handle 10 so as to permit side loading of the long flexible wire 30 through the handle and through the elongated shaft 20. The transversely-extending section 16b of slot 16 terminates in a proximally-extending notch 16c effective to center wire 30 with respect to the handle, and therefore also with respect to its recess 14 and to overlie the central area of roller 15 underlying the recess.

It will thus be seen that the proximal end of notch 15c communicates with the portion of internal passageway 13 between the transverse slot section 16b and the distal end of the handle via an opening 13a at the proximal end of the notch. It will also be seen that the distal side of recess 14 communicates with the interior portion of passageway 13 between the recess and the distal end of the handle via an opening 13b.

The Shield Member 40

The illustrated implement further includes a shield member 40 (FIGS. 7-9) within the proximal end of the handle 10, which covers the longitudinal section 16a of slot 16 formed in the handle. The shield member 40 is effective to permit the long flexible wire 30 to be passed inwardly through slot section 16a into the internal passageway 13 of handle 10, but to block the passage of the long flexible wire outwardly from the internal passageway of the handle via slot 16.

Figure 7:
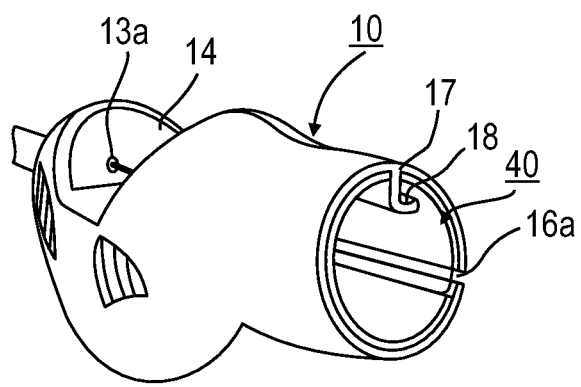
FIG. 7 is a 3-dimensional view illustrating the proximal end of the handle, particularly the provision of a shield member to facilitate side-loading the implement.
Figures 8, 9:
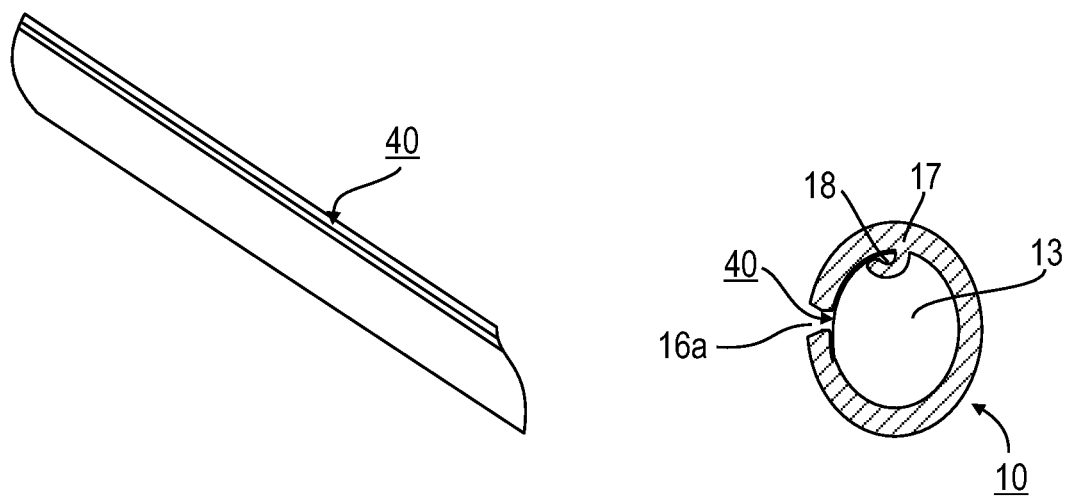
FIG. 8 is a sectional view of the proximal end of the handle and particularly showing the shield member.
FIG. 9 illustrates the shield member.

As shown particularly in FIGS. 7 and 8, the internal surface of handle 10 is formed with a hook formation 17 extending longitudinally of the handle. One edge of hook formation 17 is open, as shown at 18, for receiving a bead formed in one edge of the shield 40. Shield 40 is of a length to extend the complete length of handle 10 to its transversely-extending slot 16b, and is of a width to overlie the longitudinal section 16a of slot 16 when the opposite beaded edge of the shield is snapped into the space 18 of hook formation 17. Shield 40 is made of an elastic material allowing it to deflect inwardly, in order to permit the long flexible wire to be passed through slot 16 into internal passageway 13 for loading the wire into the implement, but to block the removal of the wire via the slot.

Use and Operation

The manner of loading the implement with the long flexible wire 30, and of using the implement for passing sutures through tissue, will now be described, particularly with reference to FIGS. 10a-10d.

Figure 10A:
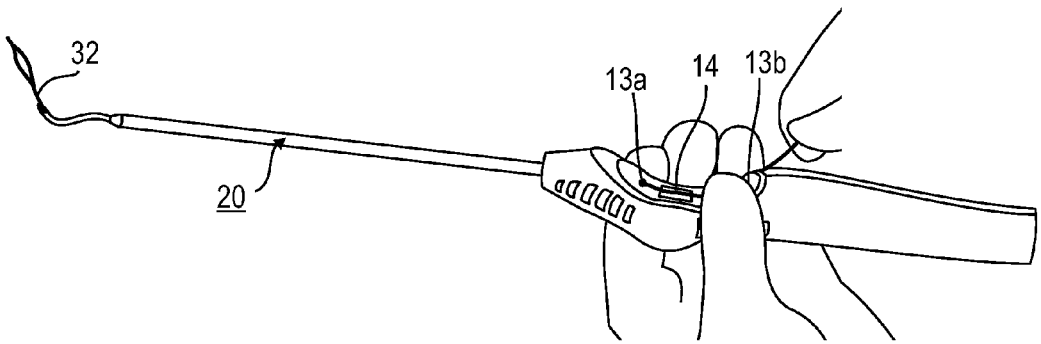
FIGS. 10A-10D illustrate the method of loading the implement with a long flexible wire formed at its distal end with a loop for receiving a suture to be passed through tissue.
Figure 10B:
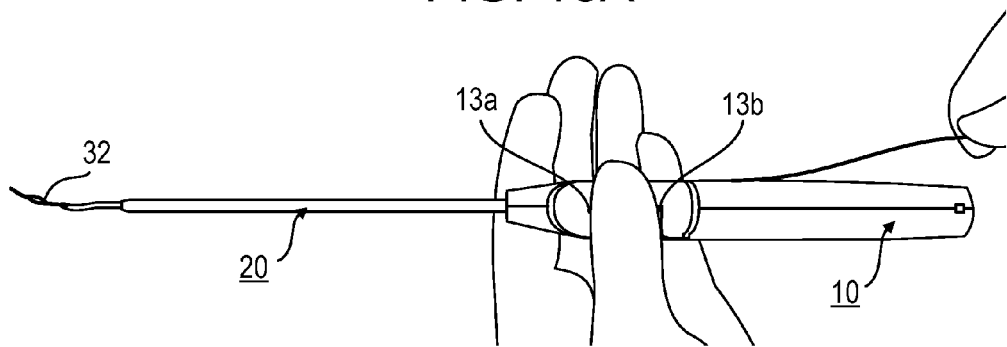
Figure 10C:
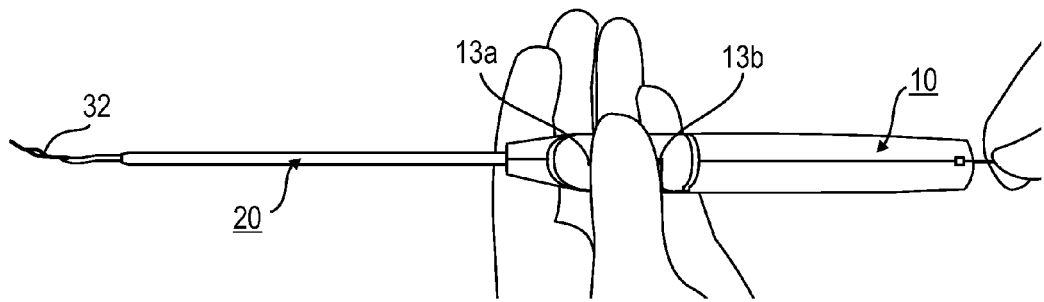
Figure 10D:
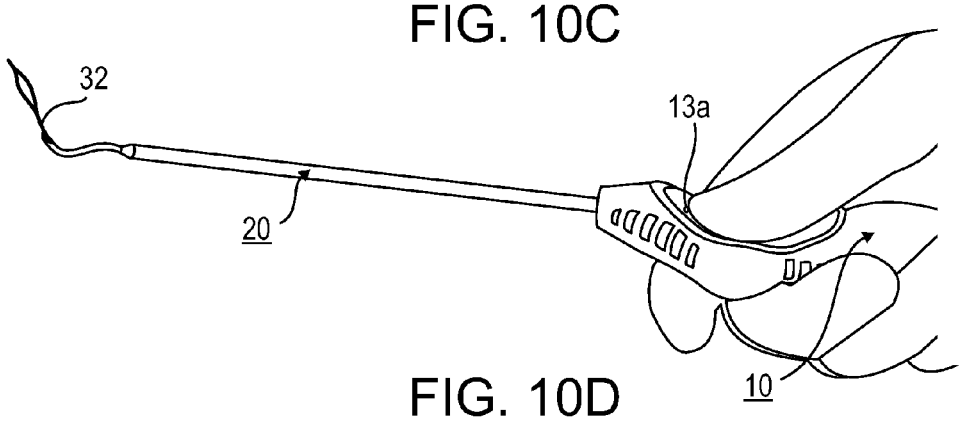

Thus, as shown in FIG. 10a, the loop 32 at the distal end of the flexible wire 30 is inserted into opening 13b of passageway 13 at the distal side of the recess 14 to overlie the roller 15. The wire is then manually advanced distally through the passageway, and through the elongated shaft 20, by thumb pressing the intermediate portion 33 of the wire against roller 15, while moving the thumb in order to advance the wire within the hollow shaft 20. The user then, with one hand, presses the wire against roller 15 in order to temporarily immobilize the wire, while the other hand side-loads the proximal end of the wire into the section of the interior passageway 13 between slot section 16b and the proximal end of the handle. This is done by passing the proximal end of the wire through the longitudinal slot section 16a into the transversely-extending slot section 16b, and then into notch 16c of the slot terminating in opening 13b. The notch centers the wire with respect to the handle recess 14 and the roller 15 underlying the recess (FIG. 10b), while the proximal end of the wire extends through the proximal end of the passageway 13 in the handle 10 (FIG. 10c).

The implement is thus loaded (FIG. 10d) such that thumb-pressing portion 33 of the wire, exposed in recess 14, and moving the thumb forwardly will project the distal loop 32 of the wire, outwardly of elongated shaft 20, while moving the thumb in the opposite direction will retract the loop within the elongated shaft.

As described earlier, shield 40 is effective to permit the long flexible wire 30 to be passed through slot section 16a inwardly into the internal passageway 13 of handle 10, but to block the passage of the long flexible wire outwardly from the internal passageway of the handle via slot 16. Thus, shield 40 facilitates the manual side-loading of the long flexible wire 30 into passageway 13 of handle 10, but once loaded, the wire can be removed from the handle only by releasing the gripping of the wire between the user's thumb and roller 15, and then moving the handle outwardly while the proximal end of the wire is passed through the proximal end 11 of the handle.

When the illustrated implement is used for passing a suture through tissue, the implement is inserted through a portal at the surgical site; and the tissue to be sutured is then pierced with the sharp distal tip 22 (FIG. 5) of the elongated shaft 20. The wire is then advanced by rotating roller 15, while the intermediate wire portion 33 is pressed against the outer surface of the roller, until loop 32 of the distal tip protrudes outwardly of the sharpened tip 22 of shaft 20, as shown in FIG. 5.

A suture manipulating device may then be used to thread the suture into the loop 32. When this is done, the wire is then retracted into the shaft 20 until the suture is held against the distal end of the shaft. The distal end of shaft 20, with the suture held to it, is then passed through the tissue.

The implement, with the suture held to the distal tip of the shaft 20, may then be passed through the portal to the outside, and the suture freed from the loop for knotting. Alternatively, once the suture is passed through the tissue, the suture may be released from the implement, by releasing the pressure applied against portion 14 of the wire, to remove the implement from the suture, if so convenient to the surgeon.

Some Variations

FIGS. 10a-10g illustrate various helical, corkscrew, or other curved arrangements, shown at 22a-22g respectively, that may be formed at the distal end of the elongated shaft 20 in order to facilitate piercing of tissue at any relative orientation to the elongated shaft when inserted via the portal opening into the patient's body. Such variations in the distal sharpened tip of the elongated shaft may be provided in a set of implements constructed with such distal tips, or may be included as attachments to the distal end of the elongated shaft.

While the invention has been described with respect to one preferred embodiment, it will be appreciated that this is set forth merely for purposes of example, and that many other variations, modifications and applications of the invention may be made.

What is claimed is:

1. A medical implement, comprising:
   a handle having a slot extending longitudinally through the handle from its outer surface to an internal passageway for side-loading the handle, in respect to a top of the handle, with a manipulatable member in the form of an elongated wire suitable for shuttling a suture;
   and a shield located within said passageway; said shield extending longitudinally in the handle along a longitudinal section of said slot and including an elastic section normally covering said slot; said elastic section of the shield being yieldable to permit side-loading of said wire into the passageway, but preventing said side-loaded wire from passing outwardly from said internal passageway wherein the implement further comprises a shaft having a proximal end joined to a distal end of the handle, a distal end suitable for insertion into the body during surgery, said distal end formed with an opening, and a passageway from said proximal end of said shaft to said distal end of the said shaft for passing of said wire through.

2. The implement according to claim 1, wherein the handle includes a hook formation extending longitudinally in the internal surface of the handle and open at one side for receiving and securing said one edge of the shield within the handle.

3. The implement according to claim 2,
   wherein the handle further includes an intermediate portion formed with a recess extending from its outer surface to the internal passageway;
   wherein the wire forms a part of a shuttle comprising a suture-receiving element, said shuttle movable through the passageway and having an intermediate portion within the recess and exposed for manipulation by a user;
   and wherein the implement further comprises a roller rotatably mounted to the handle underlying the exposed intermediate portion of the shuttle such that, after the suture has been received by the suture-receiving element of the shuttle, a user, while gripping the handle, may manipulate the shuttle with respect to the distal end of the handle, by thumb-pressing the intermediate portion of the shuttle against the roller and rotating the roller.

4. The implement according to claim 3, wherein, the distal end of the shaft is formed with a pointed tip for piercing the tissue.

5. The implement according to claim 4, wherein the shuttle includes a proximal end extending outwardly of the proximal end of the handle, and a distal end formed with a loop defining the suture-receiving element and extending outwardly of the distal end of the shaft.

6. The implement according to claim 5, wherein said wire for a of said shuttle is flexible, and includes two strands formed at its distal end with the loop.

7. The implement according to claim 1, wherein the handle further includes an intermediate portion formed with a recess extending from its outer surface to the internal passageway;
   wherein said wire forms a part of a shuttle comprising a suture-receiving element, a movable through the passageway and having an intermediate portion within the recess and exposed for manipulation by a user;
   and wherein the implement further comprises a roller rotatably mounted to the handle underlying the exposed intermediate portion of the shuttle such that, after the suture has been received by the suture-receiving element of the shuttle, a user, while gripping the handle, may manipulate the shuttle with respect to the distal end of the handle, by thumb-pressing the intermediate portion of the shuttle against the roller and rotating the roller.

8. The implement according to claim 7, wherein said shuttle includes a proximal end extending outwardly of the proximal end of the handle, and a distal end formed with a loop defining the suture-receiving element and extending outwardly of the distal end of the shaft.

9. The implement according to claim 8, wherein said wire forming a part of said shuttle is flexible, and includes two strands formed at its distal end with the loop.

10. The implement according to claim 1, wherein the slot terminates in a transversely-extending section having a proximally-extending notch effective to center the wire with respect to handle, and therefore also with respect to the recess therein.

11. The implement according to claim 1, wherein said elastic section of the shield deflects inwardly into said passageway.

12. The implement according to claim 1, wherein said passageway is configured for receiving said wire, such that said wire is freely movable within said passageway along a longitudinal axis of said passageway.

13. The implement according to claim 1, wherein said handle further comprises a recess extending longitudinally in the internal surface of the handle for receiving a free edge of said elastic section of said shield.

14. The implement according to claim 1, wherein at least one edge of said shield is curved.

* * * * *